(12) United States Patent
Alisi et al.

(10) Patent No.: US 7,879,900 B2
(45) Date of Patent: Feb. 1, 2011

(54) 3-AMINOCARBAZOLE COMPOUNDS, PHARMACEUTICAL COMPOSITION CONTAINING THE SAME AND METHOD FOR THE PREPARATION THEREOF

(75) Inventors: Maria Alessandra Alisi, Rome (IT); Patrizia Dragone, Rome (IT); Guido Furlotti, Rome (IT); Nicola Cazzolla, Albano Laziale (IT); Vincenzo Russo, Altomonte (IT); Giorgina Mangano, Rome (IT); Isabella Coletta, Rome (IT); Lorenzo Polenzani, Grottaferrata (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 11/916,487

(22) PCT Filed: Jul. 25, 2006

(86) PCT No.: PCT/EP2006/007393

§ 371 (c)(1),
(2), (4) Date: Dec. 4, 2007

(87) PCT Pub. No.: WO2007/014687

PCT Pub. Date: Feb. 8, 2007

(65) Prior Publication Data

US 2008/0207727 A1    Aug. 28, 2008

(30) Foreign Application Priority Data

Aug. 3, 2005   (IT) .......................... MI2005A1523

(51) Int. Cl.
*A61K 31/403* (2006.01)
*C07D 209/88* (2006.01)
(52) U.S. Cl. .................... 514/411; 548/440; 548/444
(58) Field of Classification Search ................. 514/411; 548/440
See application file for complete search history.

(56) References Cited

U.S. PATENT DOCUMENTS 6,399,631 B1    6/2002   Elliot et al.

FOREIGN PATENT DOCUMENTS

| EP | 0 310 179 | 4/1989 |
|----|-----------|--------|
| WO | WO 01/07409 A1 | 2/2001 |
| WO | WO 02/051806 A1 | 7/2002 |
| WO | 02/096902 | 12/2002 |

OTHER PUBLICATIONS

Lala et al., Role of nitric oxide in tumor progression: Lessons from experimental tumors, Cancer and Metastasis Reviews (1998), 17, 91-106.*

Golub et al., Molecular Classification of Cancer: Class Discovery and Class Prediction by Gene Expression Monitoring, Science (1999), vol. 286, 531-537.*
Antonio R. Damasio, Alzheimer's Disease and Related Dementias, Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL: http://www.cnn.com/2003/HEALTH/conditions/O9/24/alzheimers.drug.ap/index.html, pp. 1 and 2.*
Patani et al., Bioisosterism: A Rational Approach in Drug Design, 1996, Chem. Rev., 96, 3147-3176.*
Joseph P. Portanova, et al., "Selective Neutralization of Prostaglandin $E_2$Blocks Inflammation, Hyperalgesia, and Interleukin 6 Production in Vivo", J. Exp. Med., vol. 184, Sep. 1996, pp. 883-891.
Akinori Ueno, et al., "Major roles of prostanoid receptors IP and $EP_3$ in endotoxin-induced enhancement of pain perception", Biochemical Pharmacology, vol. 62, 2001, pp. 157-160.
Fumitaka Ushikubi, et al., "Impaired febrile response in mice lacking the prostaglandin E receptor subtype $EP_3$," Nature, vol. 395, Sep. 17, 1998, pp. 281-284.
Garret A. Fitzgerald, M.D., et al., "The coxibs, Selective Inhibitors of Cyclooxygenase-2", The New England Journal Medicine, vol. 345, No. 6, Aug. 9, 2001, pp. 433-442.
Samir Malhotra, M. D., et al., "COX-2 Inhibitors: A Class Act or Just VIGORously Promoted", http://www.medscape.com/viewarticle/470342 print, Medscpe General Medicine, vol. 6, No. 1, 2004, pp. 1-5.
Debabrata Mukherjee, et al., "Cardiovascular risk and COX-2 inhibitors", Arthritis Research and Therapy 2003, vol. 5, No. 1, 5:Aug. 11, 2002, pp. 8-11.

(Continued)

*Primary Examiner*—Kamal A Saeed
*Assistant Examiner*—Kristin Bianchi
(74) *Attorney, Agent, or Firm*—Oblon, Spivak, McClelland, Maier & Neustadt, L.L.P.

(57) ABSTRACT

A compound of formula (I), in which R1, R2, R3, R4, R5, R6, X and Y have the meanings indicated in the description, and the pharmaceutically acceptable salts thereof. A pharmaceutical composition containing a compound of formula (I) or a pharmaceutically acceptable salt thereof. A method for preparing the abovementioned compound of formula (I) and the pharmaceutically acceptable salts thereof.

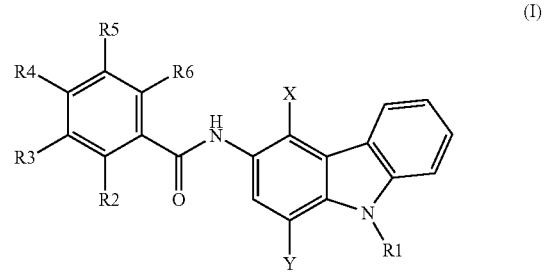

22 Claims, 1 Drawing Sheet

OTHER PUBLICATIONS

Michael H. Block, et al., "Discovery and Optimization of a Series of Carbazole Ureas as NPY5 Antagonists for the Treatment of Obesity", J. Med. Chem., vol. 45, 2002, pp. 3509-3523.

Jean-Charles Lancelot, et al., "Efficient Synthesis of 6H-Pyrido [3,2-b] Carbazole Derivatives from 3-Amino-1,4-Dimethyl Carbazole", Chem. Pharm. Bull., vol. 35, No. 1, 1987, pp. 425-428.

Staffan Thorèn, et al., "Coordinate up- and down-regulation of glutathione-dependent prostaglandin E Synthase and cyclooxygenase-2 in A549 cells inhibition by NS-398 and leukotriene $C_4$", Eur. J. Biochem., vol. 267, 2000, pp. 6428-6434.

Jeffrey L Stock, et al., "The prostaglandin $E_2$EP1 receptor mediates pain perception and regulates blood pressure", The Journal of Clinical Investigation, vol. 107, No. 3, Feb. 2001, pp. 325-331.

George B. Zavoico, et al., IL-1 and Related Cytokines Enhance Thrombin-Stimulated $PGI_2$ Production in Cultured Endothelial Cells Without Affecting Thrombin-Stimulated von Willebrand Factor Secretion or Platelet-Activating Factor Biosynthesis, The Journal of Immunology, vol. 142, No. 11, Jun. 1, 1989, pp. 3993-3999.

U.S. Appl. No. 11/909,393, filed Sep. 21, 2007, Polenzani, et al.

* cited by examiner 8 mice/group
*p<0.05 vs vehicle treated group by ANOVA

3-AMINOCARBAZOLE COMPOUNDS, PHARMACEUTICAL COMPOSITION CONTAINING THE SAME AND METHOD FOR THE PREPARATION THEREOF

FIELD OF THE INVENTION

The present invention relates to a 3-aminocarbazole compound, to a pharmaceutical composition containing the same and to a method for the preparation thereof.

More particularly, the present invention relates to a 3-aminocarbazole compound that is useful for treating or preventing disturbances associated with the production of prostaglandin $E_2$ ($PGE_2$), for instance inflammatory processes, tumours, Alzheimer's disease and atherosclerosis.

PRIOR ART

The value of the $E_2$ prostaglandins ($PGE_2$) arises from the role that they play as bioregulators, together with other prostanoids produced metabolically from arachidonic acid, and as inflammation mediators.

Prostanoids are a class of compounds including prostaglandins, thromboxanes and prostacyclins. Prostanoids are lipid mediators that act as local hormones on the cells adjacent to the site of their release. Prostanoids are mainly produced from arachidonic acid by cyclooxygenase-activated enzymatic oxidation. Cyclooxygenases (prostaglandin G/H synthases) catalyse the sequential formation of $PGG_2$ and $PGH_2$ from arachidonic acid. $PGH_2$ is then converted by means of specific enzymes into various prostanoids. The $D_2$ prostaglandins ($PGD_2$), $E_2$ prostaglandins ($PGE_2$), $F_{2\alpha}$ prostaglandins ($PGF_{2\alpha}$), $I_2$ prostaglandins ($PGI_2$) and $A_2$ thromboxanes ($TXA_2$) are formed in this way.

With the ejection of seminal fluid, the prostanoids are not accumulated. Following various stimuli (inflammatory, immunological, hormonal, ultraviolet light, tumoral agents and also mechanical agitation), they are synthesized and released into the extracellular space, from where they pass into the plasma, the urine and other biological fluids.

Prostanoids play an important role in the defense mechanisms of the functioning of organs and in the integrity of the body. This is demonstrated by the cytoprotective function in the gastrointestinal tract, by the regulation of the renal function and of capillary circulation, by the regulation of platelet aggregation and blood clotting, the involvement in the differentiation of immune cells and in wound repair, bone metabolism and ovulation.

In particular, the vasoprotective action of the $PGI_2$ prostanoids, which are essential for maintaining vascular tonus and for preventing thromboembolism and atherosclerosis at the endothelial level, and the anti-inflammatory and antiproliferative action of the $PGD_2$ prostanoids, the metabolite of which, 15d-$PGJ_2$, is capable of exerting anti-inflammatory effects by means of activation of the PPARγ (peroxisome proliferator-activated receptor-gamma) nuclear receptors (Inoue et al., 2000), should be underlined.

Prostanoids are thus bioregulators, but also important mediators of inflammation and of other pathologies.

In particular, the $PGE_2$ prostanoids are abundant in the sites of inflammation and are responsible for various pathological aspects of acute and chronic inflammation, for instance oedema, the formation of erythemas, inflammatory pain, articular inflammation and fever. In point of fact, the $PGE_2$ prostanoids represent potent pro-inflammatory and algogenic agents. Anti-$PGE_2$ antibodies have anti-inflammatory activity and animals lacking $PGE_2$ receptors show a reduced response to inflammatory stimuli (Portanova et al., 1996, Ueno et al., 2001) and an absent febrile response to pyrogenic stimuli (Ushikubi et al., 1998).

The non-steroidal anti-inflammatory drugs (NSAIDs) and selective COX-2 drugs currently in use reduce the inflammation-related symptoms by means of the non-selective inhibition of the production of eicosanoids ($PGE_2$, $PGD_2$, $PGF_{2\alpha}$, $PGI_2$ and $TXA_2$) on account of their inhibitory action on the cyclooxygenases 1 and 2 (FitzGerald and Patrono, 2001).

In particular, the selective COX-2 drugs currently marketed have reduced gastrointestinal toxicity when compared with conventional non-steroidal anti-inflammatory drugs (NSAIDs). However, the said selective COX-2 drugs reduce the production of vascular prostacyclin ($PGI_2$, which is produced predominantly from COX-2), altering the normal equilibrium between the prothrombotic and antithrombotic eicosanoids in favour of the prothrombotic ($TXA_2$, which is produced predominantly from COX-1), and give rise to an increased risk of thrombotic-cardiovascular events (S. Malhotra, MD, DM; N. Shafiq, MD; P. Pandhi, MD Medscape General Medicine 6(1), 2004; D. Mukherjee and E. J. Topol Cardiovascular risk and COX-2 inhibitors, Arthritis Res. Ther. 2003, 5:8-11-2002).

Various 3-aminocarbazole compounds have been studied for their ability to selectively bind to the human Y5 receptor and to modulate its activity. This ability makes them useful in the treatment of appetite and metabolic disorders, for instance obesity, bulimia nervosa, anorexia nervosa, sleep disturbances, morphine dependency and epileptic attacks (WO 01/07409 A1, WO 02/051806, WO 02/096902 and U.S. Pat. No. 6,399,631).

SUMMARY OF THE INVENTION

Surprisingly, it has now been found, that certain 3-aminocarbazole compounds are capable of selectively inhibiting the production of prostaglandin $E_2$ ($PGE_2$).

These compounds are capable of reducing the production of $PGE_2$ and are thus active in all the pathological conditions in which $PGE_2$ acts as a mediator (for example: inflammatory processes, pain, fever, tumours, Alzheimer's disease and atherosclerosis).

Typical examples of such inflammatory processes are oedema, erythema, articular inflammation, rheumatoid arthritis and arthrosis.

Typical examples of such tumours are colorectal and pulmonary carcinoma and adenocarcinoma.

The compounds of the present invention selectively inhibit the synthesis of $PGE_2$. This selectivity has the advantage of inhibiting a potent mediator of inflammation, pain and fever, while leaving unaltered the production of the other prostanoids produced simultaneously in the arachidonic acid cascade, such as $PGF_{2\alpha}$, $TXA_2$, $PGI_2$ and $PGD_2$. All the defense mechanisms of the functioning of organs and of the integrity of the body that are typical of the activity of the other prostanoids thus remain unchanged.

Similarly to conventional non-steroidal anti-inflammatory drugs, the compounds of the present invention have anti-inflammatory, antipyretic and analgesic properties, and are thus active in pathologies such as inflammation, pain, fever, rheumatoid arthritis and arthrosis. In addition, since the involvement of $PGE_2$ in tumours, Alzheimer's disease and atherosclerosis is known in the literature, the compounds of the present invention also have applications in the prevention and treatment of these pathologies.

Advantageously, these compounds however show few side effects when compared with NSAIDs and selective COX-2 drugs, which, by inhibiting cyclooxygenases, do not discriminate between the prostanoids.

In particular, these derivatives are useful in both the treatment and the prevention of inflammatory processes.

In particular, the compounds of the present invention show reduced gastrointestinal, renal and vascular toxicity.

DETAILED DESCRIPTION OF THE INVENTION

Figure 1:
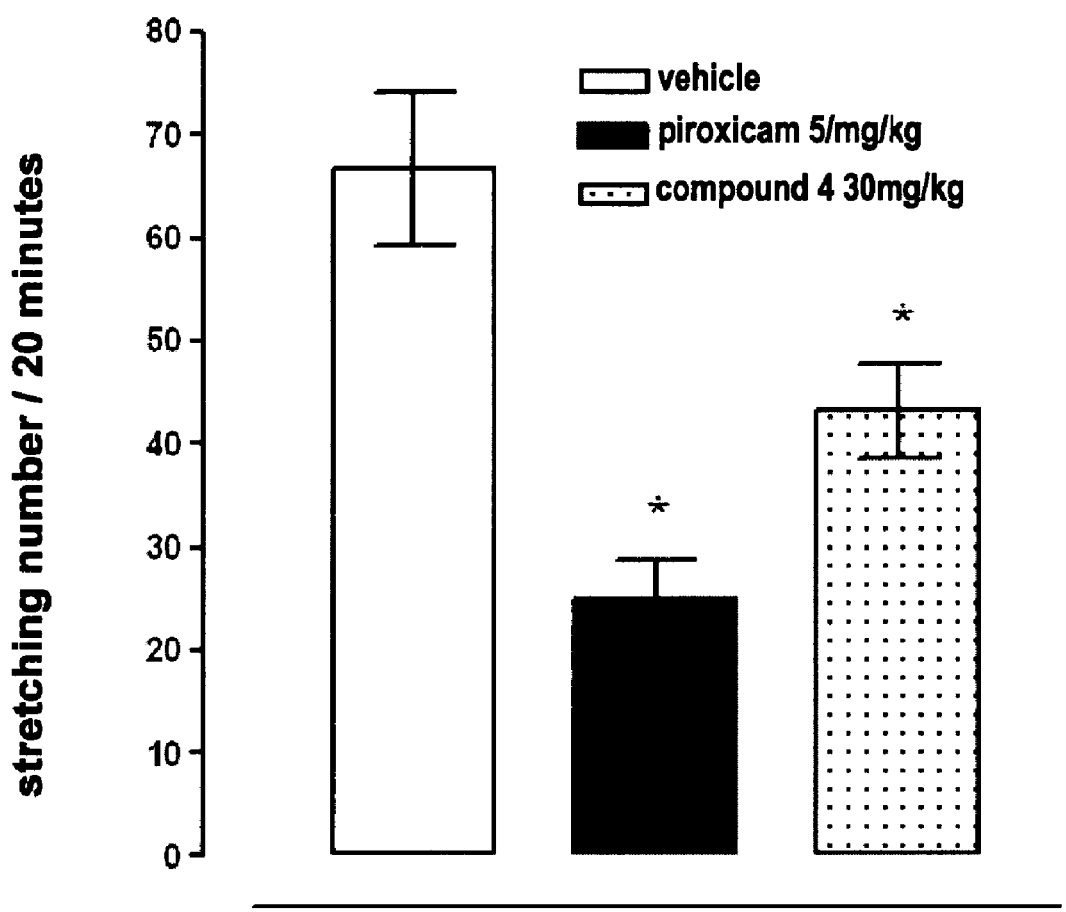
FIG. 1 is a graph depicting stretching number/20 minutes for a vehicle, piroxicam at 5/mg/kg, and compound 4 at 30 mg/kg.

In a first aspect, the present invention relates to a 3-aminocarbazole compound characterized in that it is selected from the group comprising the compounds of Table 1 below:

TABLE 1

(I)

[Chemical structure showing benzamide linked to carbazole with substituents R1-R6, X, Y]

| Compound No. | R1 | R2 | R3 | R4 | R5 | R6 | X | Y |
|---|---|---|---|---|---|---|---|---|
| 1 | $CH_3$ | Cl | H | H | H | H | H | H |
| 2 | $CH(CH_3)_2$ | Cl | H | H | H | H | H | H |
| 3 | $PhCH_2$ | Cl | H | H | H | H | H | H |
| 4 | $CH_3CH_2$ | $CF_3$ | H | H | H | H | H | H |
| 5 | $CH_3CH_2$ | $CH_3$ | H | H | H | $CH_3$ | H | H |
| 6 | $CH_3CH_2$ | F | H | H | H | $CF_3$ | H | H |
| 7 | $CH_3CH_2$ | $CF_3$ | H | F | H | H | H | H |
| 8 | $CH_3CH_2$ | Br | H | H | H | $OCH_3$ | H | H |
| 9 | $CH_3CH_2$ | Cl | H | H | Cl | $OCH_3$ | H | H |
| 10 | $PhCH_2$ | $NH_2$ | H | H | H | H | H | H |
| 11 | $CH_3CH_2$ | $N(CH_3)_2$ | H | H | H | H | H | H |
| 12 | $CH_3(CH_2)_4$ | Cl | H | H | H | H | H | H |
| 13 | $CH_3OCH_2CH_2$ | Cl | H | H | H | H | H | H |
| 14 | $HOOC(CH_2)_3$ | Cl | H | H | H | H | H | H |
| 15 | $CH_3CH_2$ | Cl | H | H | H | H | $CH_3$ | $CH_3$ |
| 16 | $CH_3CH_2$ | Cl | H | H | H | H | $CH_3$ | H |
| 17 | $CH_3CH_2$ | Cl | H | H | H | H | H | $CH_3$ |
| 18 | $CH_3CH_2$ | Cl | H | H | H | H | $CH_3$ | $OCH_3$ | and the pharmaceutically acceptable salts thereof.

As is known to those skilled in the art, the pharmaceutically acceptable salts of the compounds of Table 1 will be:

acid-addition salts when the compound is basic, for instance compound 10 or 11, or base-addition salts when the compound is acidic, for instance compound 14.

Examples of suitable pharmaceutically acceptable acids are mineral acids such as HCl, HBr, $H_2SO_4$ and $H_3PO_4$, and organic acids such as oxalic acid, tartaric acid, methanesulfonic acid, p-toluenesulfonic acid, maleic acid, succinic acid, lactic acid and citric acid.

Examples of suitable pharmaceutically acceptable bases are alkali metals and alkaline-earth metals such as $Na^+$, $K^+$, $Mg^{++}$ and $Ca^{++}$, and organic bases such as tromethamine, choline and lysine.

In a second aspect, the present invention relates to a pharmaceutical composition characterized in that it comprises a therapeutically effective dose of a 3-aminocarbazole compound selected from the group comprising the compounds of Table 1 above or a pharmaceutically acceptable salt thereof together with at least one pharmaceutically acceptable inert vehicle.

Preferably, the pharmaceutical compositions of the present invention are prepared in suitable dosage forms.

Examples of suitable dosage forms are tablets, capsules, coated tablets, granules, and solutions and syrups for oral administration; creams, ointments and antiseptic plasters for topical administration; suppositories for rectal administration and sterile solutions for administration by injection, or aerosol or ophthalmic administration.

Advantageously, these dosage forms are formulated so as to ensure a controlled release over time of a compound of Table 1 above or of a pharmaceutically acceptable salt thereof. Specifically, depending on the type of therapy, the required release time may be very short, normal or long.

The dosage forms may also contain other conventional ingredients, for instance: preserving agents, stabilizers, surfactants, buffers, salts for regulating the osmotic pressure, emulsifiers, sweeteners, dyes, flavourings and the like.

In addition, when required for particular therapies, the pharmaceutical composition of the present invention may also contain other pharmacologically active ingredients whose simultaneous administration is useful.

The amount of the compound of the present invention in the pharmaceutical composition may vary within a wide range as a function of known factors, for instance the type of disease to be treated, the severity of the disease, the body weight of the patient, the dosage form, the selected route of administration, the number of daily administrations and the efficacy of the selected compound. However, the optimum amount may be readily and routinely determined by a person skilled in the art.

Typically, the amount of compound of the present invention in the pharmaceutical composition will be such that it ensures a level of administration of between 0.0001 and 100 mg/kg/day and even more preferably between 0.01 and 10 mg/kg/day.

The dosage forms of the pharmaceutical composition of the present invention may be prepared according to techniques that are well known to pharmaceutical chemists, including mixing, granulation, tabletting, dissolution, sterilization and the like.

In a third aspect, the present invention relates to a method for treating or preventing inflammatory processes, tumours, Alzheimer's disease and atherosclerosis in mammals, comprising the administration of a therapeutically effective amount of a 3-aminocarbazole compound selected from the group comprising the compounds of Table 1 above or a pharmaceutically acceptable salt thereof to a person in need thereof.

Preferably, the inflammatory process is selected from the group comprising oedema, erythema, articular inflammation, rheumatoid arthritis and arthrosis, and the tumour is selected from the group comprising colorectal or pulmonary carcinoma and adenocarcinoma.

The 3-aminocarbazoles of Table 1 above may be prepared according to known methods, for instance by reacting an acid, or a reactive derivative thereof, with the selected amine (patent application WO 02/096902 A1, WO 02/051806, J. Med. Chem. 2002 vol. 45, pp. 3509-3523). Typical examples of reactive derivatives are acyl halides, anhydrides or esters.

In a fourth aspect, the present invention thus relates to a method for preparing a 3-aminocarbazole of Table 1 above, characterized in that it comprises the following steps:

a) reacting an amine of formula (II)

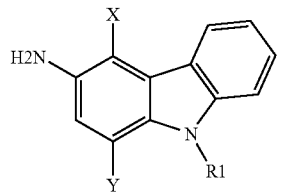

(II)

in which R1, X and Y have the meanings indicated in Table 1, with a compound of formula (III)

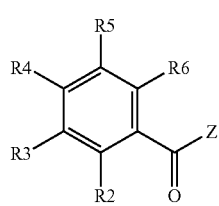

(III)

in which R2, R3, R4, R5 and R6 have the meanings indicated in Table 1, and Z is selected from the group comprising Cl, Br, OH, OR and OC(O)R, in which R is a linear or branched alkyl containing from 1 to 6 carbon atoms, to give a 3-aminocarbazole compound of formula (I)

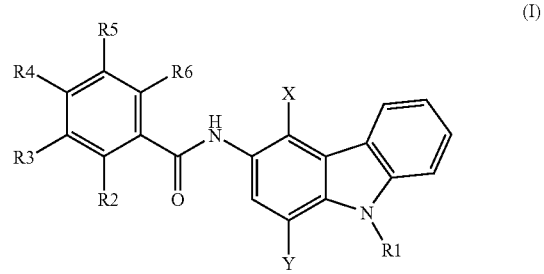

(I)

in which R1, R2, R3, R4, R5, R6, X and Y have the meanings indicated in Table 1, and b) optional formation of a pharmaceutically acceptable salt of the compound of formula (I) thus obtained.

Typically, step (a) is performed in the presence of a suitable diluent at a temperature within the range between 0 and 140° C., for a time within the range between 0.5 and 24 hours. Preferably, the reaction temperature is within the range between 15 and 40° C. Advantageously, the reaction time ranges from 2 to 18 hours.

Preferably, the diluent is aprotic, polar or apolar. Even more preferably, it is a polar aprotic diluent. Examples of suitable polar aprotic diluents are dimethylformamide and dichloromethane.

In the embodiment in which Z is Cl or Br, the reaction is advantageously performed in the presence of a suitable organic or mineral acid acceptor. Examples of suitable organic acceptors are diisopropylethylenediamine, triethyleneamine, pyridine and dimethylaminopyridine. Examples of suitable mineral acceptors are alkali metal carbonates or bicarbonates.

In the embodiment in which Z is OH, the reaction is preferably performed in the presence of a suitable coupling agent, for instance dicyclohexylcarbodiimide (also supported on polystyrene resin) or carbonyldiimidazole.

The examples that follow are given to illustrate the invention in greater detail without, however, limiting it.

EXAMPLE 1

Preparation of Compound 1

R1=CH$_3$, R2=Cl, R3=R4=R5=R6=X=Y=H a) 9-methyl-9H-carbazole

To a solution of carbazole (5 g; 0.030 mol) in dimethylformamide (50 ml) was added portionwise sodium hydride (60% suspension in mineral oil, 1.15 g; 0.030 mol) and the suspension obtained was stirred at room temperature for 0.5 hour. Iodomethane (1.43 ml; 0.030 mol) was then added dropwise.

The suspension thus obtained was stirred for 16 hours and H$_2$O was then added cautiously until precipitation was complete. The precipitate was collected by filtration under vacuum and dried in a vacuum oven.

5.3 g of the desired product were thus obtained and were used without further purification.

¹H NMR (300 MHz, DMSO-d₆) δ ppm 3.87 (s, 3 H), 7.20 (t, J=7.5 Hz, 2 H), 7.43-7.49 (m, 2 H), 7.56-7.61 (m, 2 H), 8.15 (d, J=7.5 Hz, 2 H).

b) 9-methyl-3-nitro-9H-carbazole

The product obtained as described in step a) above (3.9 g; 0.022 mol) was dissolved in glacial acetic acid (70 ml). A mixture containing fuming nitric acid (1.05 ml) in glacial acetic acid (3.11 ml) was then added dropwise over 30 minutes.

The solution thus obtained was stirred for a further 30 minutes. The reaction mixture was then poured into $H_2O$ and ice, stirred for 15 minutes and filtered. The residue thus obtained (4 g) was purified by flash chromatography, eluting with an 85/15 hexane/ethyl acetate mixture.

The desired product (2.2 g) was thus obtained.

¹H NMR (300 MHz, chloroform-d) δ ppm 3.92 (s, 3 H), 7.27-7.51 (m, 3 H), 7.54-7.63 (m, 1 H), 8.15 (d, J=7.9 Hz, 1 H), 8.40 (dd, J=8.9, 2.2 Hz, 1 H), 9.01 (d, J=2.0 Hz, 1 H).

c) 9-methyl-9H-carbazole-3-amine

The product obtained as described in step b) above (1.94 g; 0.009 mol) was dissolved in absolute ethanol (20 ml). Stannous chloride dihydrate (8.16 g; 0.043 mol) was then added. The mixture thus obtained was refluxed for 16 hours.

The reaction mixture was cooled to room temperature and the solvent was then removed under reduced pressure. The residue was taken up in $H_2O$. The pH was brought to 7.5 by adding saturated sodium bicarbonate solution and the mixture was transferred into a separating funnel. The organic phase was extracted with ethyl acetate (2×100 ml). The organic extracts were combined and washed with water saturated with NaCl (2×100 ml). The organic phase was separated out and dried over $Na_2SO_4$. The organic phase was separated out and dried over $Na_2SO_4$. The solvent was then removed by evaporation under reduced pressure and the residue thus obtained (1.5 g) was used without further purification.

¹H NMR (300 MHz, DMSO-d₆) δ ppm 3.76 (s, 3 H), 4.72 (br, s, 2 H), 6.84 (dd, J=8.8, 2.0 Hz, 1 H), 7.04-7.11 (m, 1 H), 7.25-7.30 (m, 2 H), 7.32-7.39 (m, 1 H), 7.44 (d, J=8.1 Hz, 1 H), 7.93 (dt, J=7.6, 1.0 Hz, 1 H).

d) 2-chloro-N-(9-methyl-9H-carbazol-3-yl)benzamide

The product obtained as described in step c) above (1.5 g; 0.008 mol) was dissolved in dichloromethane (20 ml). Diisopropylethylenediamine (1.19 g; 0.009 mol) and 2-chlorobenzoyl chloride (1.16 ml; 0.009 mol) were then added to the solution. The mixture thus obtained was stirred for 3 hours.

The reaction mixture was transferred into a separating funnel and washed with 1N HCl solution (50 ml), with 1N NaOH (50 ml) and with $H_2O$ (50 ml). The organic phase was separated out and dried over $Na_2SO_4$. The solvent was then removed by evaporation under reduced pressure and the residue thus obtained (3 g) was crystallized from a 1/2 hexane/ethyl acetate mixture.

2-Chloro-N-(9-methyl-9H-carbazol-3-yl)benzamide (1.2 g) was thus obtained.

m.p.: 206° C.

Elemental analysis for $C_{20}H_{15}ClN_2O$

|  | C | H | N |
|---|---|---|---|
| Found % | 71.81 | 4.34 | 8.37 |
| Calculated % | 71.75 | 4.52 | 8.37 |

¹H NMR (300 MHz, DMSO-d₆) δ ppm 3.88 (s, 3 H), 7.20 (t, J=6.9 Hz, 1 H), 7.43-7.73 (m, 8 H), 8.09 (d, J=7.6 Hz, 1 H), 8.57 (d, J=1.7 Hz, 1 H), 10.48 (br, s, 1 H).

EXAMPLE 2

Preparation of Compound 2

R1=CH(CH₃)₂, R2=Cl, R3=R4=R5=R6=X=Y=H a) 9-(1-methylethyl)-9H-carbazole

Carbazole (5 g; 0.03 mol) was reacted with isopropyl bromide (5.61 ml; 0.06 mol) by working in a manner similar to that described in Example 1a).

The solid product obtained after filtration (4 g) was purified by flash chromatography, eluting with a 97/3 hexane/ethyl acetate mixture to give 3.3 g of the desired product.

¹H NMR (300 MHz, DMSO-d₆) δ ppm, 1.63 (d, J=7.0 Hz, 6 H), 5.11 (hept, J=7.0, Hz, 1 H), 7.18 (t, J=7.5 Hz, 2 H), 7.38-7.45 (m, 2 H), 7.69 (d, J=8.2 Hz, 2 H), 8.15 (dt, J=7.6, 1.0 Hz, 2 H).

b) 9-(1-methylethyl)-3-nitro-9H-carbazole

The product obtained as described in step a) above (3.3 g; 0.016 mol) was reacted by working in a manner similar to that described in Example 1b).

The solid product obtained after filtration (3.7 g) was purified by flash chromatography, eluting with a 95/5 hexane/ethyl acetate mixture to give 1.8 g of the desired product.

¹H NMR (300 MHz, DMSO-d₆) δ ppm, 1.67 (d, J=7.0 Hz, 6 H), 5.23 (hept, J=7.0, Hz, 6 H), 7.33 (t, J=7.0 Hz, 1 H), 7.53-7.60 (m, 1 H), 7.85 (d, J=8.0 Hz, 1 H), 7.90 (d, J=9.2 Hz, 1 H), 8.31 (dd, J=9.2, 2.3 Hz, 1 H), 8.43 (dq, J=8.0, 0.7 Hz, 1 H), 9.18 (d, J=2.3 Hz, 1 H).

c) 9-(1-methylethyl)-9H-carbazole-3-amine

The product obtained as described in step b) above (1.7 g; 0.007 mol) was reacted by working in a manner similar to that described in Example 1c).

The product thus obtained (1.3 g) was used without further purification.

¹H NMR (300 MHz, DMSO-d₆) δ ppm 1.57 (d, J=7.0 Hz, 6 H), 4.71 (br, s, 2 H), 4.95 (hept, J=7.0 Hz, 1 H), 6.80 (dd, J=8.6, 2.2 Hz, 1 H), 7.04 (t, J=6.9 Hz, 1 H), 7.25-7.34 (m, 2 H), 7.38 (d, J=8.8 Hz, 1 H), 7.53 (d, J=8.6 Hz, 1 H), 7.92 (dq, J=7.8, 0.7 Hz, 1 H).

d) 2-chloro-N-[9-(1-methylethyl)-9H-carbazol-3-yl]benzamide

The product obtained as described in step c) above (1.2 g; 0.005 mol) was reacted by working in a manner similar to that described in Example 1d).

The product thus obtained (2.2 g) was crystallized twice from a 1/9 hexane/ethyl acetate mixture.

2-Chloro-N-[9-(1-methylethyl)-9H-carbazol-3-yl]benzamide (1.1 g) was thus obtained.

m.p.: 195° C.

Elemental analysis
for $C_{22}H_{19}ClN_2O$

|  | C | H | N |
|---|---|---|---|
| Found % | 72.71 | 5.16 | 7.88 |
| Calculated % | 72.82 | 5.28 | 7.72 |

$^1$H NMR (300 MHz, DMSO-$d_6$) δ ppm 1.63 (d, J=6.9 Hz, 6 H), 5.09 (hept, J=6.9 Hz, 1 H), 7.18 (t, J=7.4 Hz, 1 H), 7.38-7.73 (m, 8 H), 8.08 (d, J=7.3 Hz, 1 H), 8.56 (d, J=1.7 Hz, 1 H), 10.47 (br, s, 1 H).

EXAMPLE 3

Preparation of Compound 3

R1=CH$_2$Ph, R2=Cl, R3=R4=R5=R6=X=Y=H a) 9-(phenylmethyl)-9H-carbazole

Carbazole (5 g; 0.03 mol) was reacted with benzyl bromide (7.11 ml; 0.06 mol) by working in a manner similar to that described in Example 1a).

The solid product obtained after filtration (8 g) washed with hexane to give 7.2 g of the desired product.

$^1$H NMR (300 MHz, DMSO-$d_6$) δ ppm 5.66 (s, 2 H), 7.13-7.47 (m, 9 H), 7.62 (d, J=8.2 Hz, 2 H), 8.18 (d, J=7.6 Hz, 2 H).

b) 3-nitro-9-(phenylmethyl)-9H-carbazole

The product obtained as described in step a) above (6.7 g; 0.026 mol) was reacted by working in a manner similar to that described in Example 1b).

The solid product obtained after filtration (7 g) was purified by flash chromatography, eluting with a 95/5 hexane/ethyl acetate mixture to give 2.5 g of the desired product.

$^1$H NMR (300 MHz, DMSO-$d_6$) δ ppm 5.78 (s, 2 H), 7.15-7.39 (m, 6H), 7.52-7.60 (m, 1 H), 7.75 (d, J=8.5 Hz, 1 H), 7.85 (d, J=9.1 Hz, 1H), 8.34 (dd, J=9.1, 2.3 Hz, 1 H), 8.45 (d, J=7.3 Hz, 1 H), 9.22 (d, J=2.3 Hz, 1 H).

c) 9-(phenylmethyl)-9H-carbazole-3-amine

The product obtained as described in step b) above (1 g; 0.003 mol) was reacted by working in a manner similar to that described in Example 1c).

The product thus obtained (1 g) was used without further purification.

$^1$H NMR (300 MHz, DMSO-$d_6$) δ ppm 4.75 (br, s, 2 H), 5.52 (s, 2 H), 6.79 (dd, J=8.6, 2.2 Hz, 1 H), 7.05-7.36 (m, 9 H), 7.48 (d, J=8.5 Hz, 1 H), 7.95 (d, J=7.3 Hz, 1 H).

d) 2-chloro-N-[9-(phenylmethyl)-9H-carbazol-3-yl]benzamide

The product obtained as described in step c) above (0.9 g; 0.003 mol) was reacted by working in a manner similar to that described in Example 1d).

The product thus obtained (1.5 g) was crystallized from ethyl acetate.

2-Chloro-N-[9-(phenylmethyl)-9H-carbazol-3-yl)benzamide (550 mg) was thus obtained.

$^1$H NMR (300 MHz, DMSO-$d_6$) δ ppm 5.66 (s, 2 H), 7.11-7.31 (m, 6H), 7.39-7.68 (m, 8 H), 8.12 (d, J=7.6 Hz, 1 H), 8.59 (d, J=1.4 Hz, 1 H), 10.48 (br, s, 1 H).

EXAMPLE 4

Preparation of Compound 4

R1=CH$_3$CH$_2$, R2=CF$_3$, R3=R4=R5=R6=X=Y=H a) N-(9-ethyl-9H-carbazol-3-yl)-2-(trifluoromethyl)benzamide

To a solution of 3-amino-9-ethylcarbazole (4 g; 0.019 mol) in dichloromethane (30 ml) were added triethylamine (2.9 ml; 0.021 mol) and 2-(trifluoromethyl)benzoyl chloride (3.1 ml; 0.021 mol). The mixture thus obtained was stirred for 16 hours.

The reaction mixture was transferred into a separating funnel and washed with H$_2$O (2×50 ml). The organic phase was separated out and dried over Na$_2$SO$_4$, the solvent was removed by evaporation under reduced pressure and the residue thus obtained (4 g) was crystallized from ethanol.

N-(9-Ethyl-9H-carbazol-3-yl)-2-(trifluoromethyl)benzamide (3.5 g) was thus obtained.

m.p.: 206-207° C.

Elemental analysis
for $C_{22}H_{17}F_3N_2O$

|  | C | H | N |
|---|---|---|---|
| Found % | 68.87 | 4.26 | 7.30 |
| Calculated % | 69.01 | 4.48 | 7.33 |

$^1$H NMR (300 MHz, DMSO-$d_6$) δ ppm 1.32 (t, J=7.1 Hz, 3 H), 4.44 (q, J=7.1 Hz, 2 H), 7.16-7.23 (m, 1 H), 7.42-7.50 (m, 1 H), 7.55-7.90 (m, 7 H), 8.09 (d, J=7.7 Hz, 1 H), 8.51 (d, J=1.2 Hz, 1 H), 10.53 (br, s, 1 H).

EXAMPLE 5

Preparation of Compound 5

R1=CH$_3$CH$_2$, R2=R6=CH$_3$, R3=R4=R5=X=Y=H a) 2,6-Dimethylbenzoyl chloride

To a mixture of 2,6-dimethylbenzoic acid (3 g; 0.02 mol) in toluene (50 ml) was added thionyl chloride (3.6 ml; 0.05 mol). The mixture thus obtained was refluxed for 2 hours. The solvent and the excess thionyl chloride were then evaporated off under reduced pressure. The residue thus obtained was taken up in toluene (50 ml) three times and evaporated under reduced pressure. The product thus obtained (3.6 g) was used without further purification.

b) N-(9-ethyl-9H-carbazol-3-yl)-2,6-dimethylbenzamide

The product obtained as described in step a) above (3.3 g; 0.020 mol) was reacted by working in a manner similar to that described in Example 4.

The product obtained (2.4 g) was crystallized from isopropanol. N-(9-Ethyl-9H-carbazol-3-yl)-2,6-dimethylbenzamide (1.4 g) was thus obtained.

m.p.: 192-193° C.

Elemental analysis
for $C_{23}H_{22}N_2O$

|  | C | H | N |
|---|---|---|---|
| Found % | 80.57 | 6.48 | 8.16 |
| Calculated % | 80.67 | 6.48 | 8.18 |

$^1$H NMR (300 MHz, DMSO-$d_6$) δ ppm 1.31 (t, J=7.1 Hz, 3 H), 2.34 (s, 6 H), 4.43 (q, J=7.1 Hz, 2 H), 7.08-7.27 (m, 4 H), 7.41-7.49 (m, 1 H), 7.54-7.62 (m, 2 H), 7.68 (dd, J=8.8, 1.8 Hz, 1 H), 8.10 (d, J=7.6 Hz, 1 H), 8.59 (d, J=1.8 Hz, 1 H), 10.34 (br, s, 1 H).

EXAMPLES 6-9

Preparation of Compounds 6-9

A suspension containing 9-ethyl-3-aminocarbazole (0.1 g; 0.48 mmol) and the appropriate benzoic acid (0.70 mmol) in which R2, R3, R4, R5 and R6 have the meanings indicated in Table 1, in dichloromethane (4 ml) and DMF (0.8 ml), was stirred for 10 minutes.

Polystyrene-divinylbenzene carbodiimide resin (PS-carbodiimide) (0.73 g; 0.9 mmol) was added to the reaction mixture thus obtained, under an inert atmosphere.

The suspension was then stirred for 16 hours.

The reaction mixture was filtered and the solid product obtained was washed with dichloromethane. The solution was then treated with Amberlyst 15 resin (200 mg; 0.8 mmol) and Amberlyst A21 resin (250 mg; 1 mmol) and stirred for 2 hours. The resins were separated out by filtration and washed with dichloromethane (2×5 ml) and the organic solvent was evaporated off under reduced pressure to give the desired product.

| Compound No. | M.W. | Yield (mg) | LC/MS (M + H)$^+$ |
|---|---|---|---|
| 6 | 400.38 | 51 | 401.3 |
| 7 | 400.38 | 129 | 401.3 |
| 8 | 423.31 | 80 | 423.2 |
| 9 | 413.31 | 18 | 413.1 |

EXAMPLE 10

Preparation of Compound 10

R1=PhCH$_2$, R2=NH$_2$, X=R3=R4=R5=R6=Y=H a) 2-[(terbuthoxycarbonyl)amino]benzoic acid A mixture of anthranilic acid (6.8 g; 0.050 mol), diterbutyl dicarbonate (16.4 ml; 0.071 mol), 0.5N NaOH (100 ml), dioxan (50 ml) and acetonitrile (10 ml), was kept under stirring at room temperature for 16 hours. The solvent was removed by evaporation under reduced pressure and the residue was treated with a mixture of 100 g of ice and 100 ml of a 10% aqueous solution of citric acid. The solution was extracted with ethyl acetate (3×100 ml). The combined organic phases were washed with a saturate solution of NaCl (50 ml) and then dried on Na$_2$SO$_4$.

After filtration the solvent was removed by evaporation under reduced pressure. The thus obtained residue was crystallized from a mixture of hexane:ethyl acetate=3:1 to yield the product of the title (4.9 g).

1H NMR (300 MHz, DMSO-$d_6$) δ ppm 1.49 (s, 9 H), 7.07 (td, J=7.80, 7.50, 1.20 Hz, 1 H), 7.57 (td, J=8.53, 7.22, 1.82 Hz, 1 H), 7.96 (dd, J=7.97, 1.72 Hz, 1 H), 8.28 (dd, J=8.58, 0.91 Hz, 1 H), 10.51 (s, 1 H), 13.55 (br. s., 1 H).

b) 2-amino-N-(9-benzyl-9H-carbazol-3-yl)benzamide hydrochloride 4-dimethylaminopyridine (0.31 g, 0.0025 mol) and 9-(phenylmethyl)-9H-carbazol-3-amine, obtained as described in Example 3c) (0.626 g, 0.0023 mol), were added to a solution of the product obtained in the previous step a) (0.496 g, 0.0021 mol) in dichloromethane (5 ml).

The mixture was stirred at room temperature for 5 minutes, added with N,N-dicyclohexylcarbodiimide (0.475 g, 0.0023 mol) and kept under stirring at room temperature for 2 days.

Afterwards the mixture was diluted with dichloromethane (15 ml) and filtered through a silica layer. The solution washed with a 10% aqueous solution of citric acid (3×10 ml), water (2×10 ml) and a saturate solution of NaCl (10 ml), respectively. The organic phase was dried on Na$_2$SO$_4$ and the solvent was removed under reduced pressure.

The thus obtained product (1.3 g) was purified by flash chromatography by eluting with a mixture of hexane:ethyl acetate=7:3, and then crystallized from a mixture hexane:ethyl acetate=95:5.

The thus obtained product (350 mg, 0.712 mmol) was dissolved in ethyl acetate (50 ml) and treated with a solution of HCl in ethanol 3M (26 ml). The solvent was removed by evaporation under reduced pressure and the residue was crystallized from a mixture of absolute ethanol:ethyl acetate=1:1. The 2-amino-N-(9-benzyl-9H-carbazol-3-yl)benzamide hydrochloride (0.2 g) was thus obtained.

1H NMR (300 MHz, DMSO-$d_6$) δ ppm 5.66 (s, 2 H), 7.01 (t, J=7.51 Hz, 1 H), 7.08-7.50 (m, 12 H), 7.62 (d, J=8.59 Hz, 2 H), 7.70 (dd, J=8.82, 1.80 Hz, 1 H), 7.84 (dd, J=7.76, 0.99 Hz, 1 H), 8.10 (d, J=7.60 Hz, 1 H), 8.56 (d, J=1.65 Hz, 1 H), 10.34 (br. s., 1 H).

EXAMPLE 11

Preparation of Compound 11

R1=CH$_3$CH$_2$, R2=N(CH$_3$)$_2$,
R3=R4=R5=R6=X=Y=H a) 2-dimethylamino-N-(9-ethyl-9H-carbazol-3-yl)benzamide hydrochloride 3-amino-9-ethylcarbazole (0.484 g, 0.0023 mol) was reacted with N-dimethyl anthranilic acid (0.347 g, 0.0021 mol) by working in a similar manner to Example 10b.

The thus obtained product (0.9 g) was purified by flash chromatography by eluting with a mixture of hexane:ethyl acetate=8:2. Afterwards, it was dissolved in ethanol, treated with a solution of HCl in 3M ethanol (2.0 ml) and kept at room temperature for 3 hours. Then the solvent was removed under reduced pressure and the residue was crystallized from a mixture of isopropyl alcohol:isopropyl ether=1:3.

The 2-dimethylamino-N-(9-ethyl-9H-carbazol-3-yl)benzamide hydrochloride (0.25 g) was thus obtained.

1H NMR (300 MHz, DMSO-$d_6$+D$_2$O) δ ppm 1.29-1.38 (m, J=7.01, 7.01 Hz, 3 H), 3.21 (s, 6 H), 4.45 (q, J=7.16 Hz, 2 H), 7.24 (td, J=7.86, 7.05, 0.88 Hz, 1 H), 7.50 (td, J=8.26, 7.09, 1.17 Hz, 1 H), 7.56-7.69 (m, 3 H), 7.73-7.83 (m, 2 H), 7.91 (d, J=8.00 Hz, 1 H), 8.09-8.16 (m, 2 H), 8.56 (d, J=1.75 Hz, 1 H).

EXAMPLE 12

Preparation of Compound 12

R1=$CH_3(CH_2)_4$, R2=Cl, R3=R4=R5=R6=X=Y=H a) 9-pentyl-9H-carbazole

Carbazole (5 g, 0.030 mol) was reacted with 1-bromopentane (7.5 ml, 0.06 mol) by working in a similar manner to Example 1a).

The solid product obtained after cool filtration (8 g) was purified by filtration through a silica layer by eluting with a mixture of hexane:ethyl acetate=8:2.

It was thus obtained the desired product (6 g).

1H NMR (300 MHz, CHLOROFORM-d) δ ppm 0.82-0.94 (m, J=7.00, 7.00 Hz, 3 H), 1.28-1.44 (m, 4 H), 1.79-1.94 (m, 2 H), 4.28 (t, J=7.23 Hz, 2 H), 7.21 (td, J=7.86, 6.76, 1.32 Hz, 2 H), 7.36-7.49 (m, 4 H), 8.09 (d, J=7.75 Hz, 2 H).

b) 3-nitro-9-pentyl-9H-carbazole

The product obtained as described in the preceding step a) (1 g, 0.0042 mol) was reacted by working in a similar manner to Example 1b).

The thus obtained product (0.9 g) was purified by flash chromatography by eluting with a mixture of hexane:ethyl acetate=10:1 and the resulting product (0.54 g) was used without further purification.

1H NMR (300 MHz, DMSO-$d_6$) δ ppm 0.75-0.85 (m, J=7.00, 7.00 Hz, 3H), 1.19-1.37 (m, 4 H), 1.70-1.86 (m, 2 H), 4.47 (t, J=7.10 Hz, 2 H), 7.33 (td, J=7.90, 7.00, 0.80 Hz, 1 H), 7.58 (td, J=7.68, 1.16 Hz, 1 H), 7.72 (d, J=8.42 Hz, 1 H), 7.78 (d, J=9.08 Hz, 1 H), 8.33 (dd, J=9.17, 2.39 Hz, 1 H), 8.40 (d, J=7.76 Hz, 1 H), 9.17 (d, J=2.31 Hz, 1 H).

c) 9-pentyl-9H-carbazol-3-amine

The product obtained as described in the preceding step b) (2.6 g, 0.0092 mol) was reacted by working in a similar manner to Example 1c).

The thus obtained product (2 g) was purified by crystallization from hexane to yield the desired product (1.3 g).

GC/MS (m/z): 252 (molecular ion), 195 (basic peak)

d) 2-chloro-N-(9-pentyl-9H-carbazol-3-yl)benzamide

The product obtained as described in the preceding step c) (0.6 g, 0.0024 mol) was reacted by working in a similar manner to Example 1d).

The thus obtained product (0.9 g) was purified by crystallization from a mixture of hexane:ethyl acetate=4:1. The 2-chloro-N-(9-pentyl-9H-carbazol-3-yl)benzamide (0.3 g) was thus obtained.

1H NMR (300 MHz, DMSO-$d_6$) δ ppm 0.81 (t, J=7.00 Hz, 3 H), 1.21-1.36 (m, 4 H), 1.71-1.86 (m, 2 H), 4.38 (t, J=6.97 Hz, 2 H), 7.19 (td, J=7.90, 7.00, 0.80 Hz, 1 H), 7.41-7.71 (m, 8 H), 8.09 (d, J=7.49 Hz, 1H), 8.56 (d, J=1.74 Hz, 1 H), 10.47 (s, 1 H).

EXAMPLE 13

Preparation of Compound 13

R1=$CH_3OCH_2CH_2$, R2=Cl, R3=R4=R5=R6=X=Y=H a) 9-(2-methoxyethyl)-9H-carbazole

Cesium carbonate (19.5 g, 0.06 mol) was added to a solution of carbazole (5 g, 0.030 mol) in DMF (100 ml) and the mixture was kept under stirring for 1 hour at room temperature. 2-bromoethylmethylether (5.6 ml, 0.06 mol) was added and the mixture was kept under stirring at 90° C. for 5 hours.

Afterwards the reaction mixture was poured into water (300 ml) and stirred at room temperature for 2 hours. The solid (4.8 g) was filtered and used without any further purification.

1H NMR (300 MHz, DMSO-$d_6$) δ ppm 3.18 (s, 3 H), 3.71 (t, J=5.41 Hz, 2 H), 4.55 (t, J=5.41 Hz, 2 H), 7.19 (td, J=7.80, 7.10, 1.00 Hz, 2 H), 7.44 (td, J=8.26, 7.09, 1.17 Hz, 2 H), 7.60 (d, J=8.18 Hz, 2 H), 8.14 (dt, J=7.75, 0.90 Hz, 2 H).

b) 3-nitro-9-(2-methoxyethyl)-9H-carbazole

The product obtained as described in the preceding step a) (6 g, 0.027 mol) was reacted by working in a similar manner to Example 1b).

The thus obtained product (7.2 g) was purified by crystallization from toluene to yield the desired product (4.5 g).

1H NMR (300 MHz, DMSO-$d_6$) δ ppm 3.16 (s, 3 H), 3.74 (t, J=5.19 Hz, 2 H), 4.66 (t, J=5.19 Hz, 2 H), 7.33 (ddd, J=8.00, 7.00, 0.88 Hz, 1 H), 7.57 (ddd, J=8.25, 7.20, 1.17 Hz, 1 H), 7.74 (dt, J=8.18, 0.88 Hz, 1 H), 7.79 (d, J=9.06 Hz, 1 H), 8.33 (dd, J=9.21, 2.34 Hz, 1 H), 8.40 (dt, J=7.75, 0.88 Hz, 1 H), 9.16 (d, J=2.34 Hz, 1 H).

c) 9-(2-methoxyethyl)-9H-carbazol-3-amine

The product obtained as described in the preceding step b) (3 g, 0.011 mol) was reacted by working in a similar manner to Example 1c).

The thus obtained product (2.7 g) was crystallized from a mixture of hexane:ethyl acetate=2:1 to yield the desired product (1.1 g).

1H NMR (300 MHz, DMSO-$d_6$) δ ppm 3.18 (s, 3 H), 3.66 (t, J=5.55 Hz, 2 H), 4.42 (t, J=5.48 Hz, 2 H), 4.70 (s, 2 H), 6.81 (dd, J=8.48, 2.19 Hz, 1H), 7.06 (ddd, J=7.80, 7.00, 0.88 Hz, 1 H), 7.26 (d, J=1.90 Hz, 1 H), 7.29 (d, J=8.48 Hz, 1 H), 7.32 (ddd, J=8.25, 7.00, 1.25 Hz, 1 H), 7.46 (dt, J=8.25, 0.88 Hz, 1 H), 7.91 (dt, J=7.60, 0.88 Hz, 1 H).

d) 2-chloro-N-[9-(2-metoxyethyl)-9H-carbazol-3-yl]benzamide

The product obtained as described in the preceding step c) (0.58 g, 0.0024 mol) was reacted with 2-chlorobenzoyl chloride (0.36 ml, 0.0028 mol) by working in a similar manner to Example 1d).

The thus obtained product (0.9 g) was crystallized from a mixture of hexane:ethyl acetate=2:1. It was thus obtained the 2-chloro-N-[9-(2-metoxyethyl)-9H-carbazol-3-yl]benzamide (0.5 g).

1H NMR (300 MHz, DMSO-$d_6$) δ ppm 3.18 (s, 3 H), 3.72 (t, J=5.28 Hz, 2 H), 4.55 (t, J=5.37 Hz, 2 H), 7.19 (ddd, J=7.90, 7.00, 0.88 Hz, 1 H), 7.39-7.69 (m, 8 H), 8.08 (d, J=7.76 Hz, 1 H), 8.54 (d, J=1.82 Hz, 1 H), 10.47 (s, 1 H).

EXAMPLE 14

Preparation of Compound 14

R1=HOOC(CH$_2$)$_3$, R2=Cl, R3=R4=R5=R6=X=Y=H a) 4-(9H-carbazol-9-yl)butanenitrile Carbazole (10 g, 0.060 mol) was reacted with 4-bromobutyronitrile (11.9 ml, 0.12 mol) by working in a similar manner to Example 1a).

The solid product obtained after cool filtration (18 g) was purified by flash chromatography by eluting with a mixture of hexane:ethyl acetate=8:2. It was thus obtained the desired product (10 g).

1H NMR (300 MHz, DMSO-d$_6$) δ ppm 2.03-2.15 (m, J=7.23, 7.23, 7.23, 7.23 Hz, 2 H), 2.55 (t, J=7.23 Hz, 2 H), 4.46 (t, J=7.16 Hz, 2 H), 7.21 (td, J=7.86, 7.05, 1.02 Hz, 2 H), 7.47 (td, J=8.26, 7.09, 1.32 Hz, 2H), 7.62 (dt, J=8.22, 0.79 Hz, 2 H), 8.16 (dq, J=7.75, 0.73, 0.58 Hz, 2H).

b) 4-(3-nitro-9H-carbazol-9-yl)butanenitrile

The product obtained as described in the preceding step a) (5 g, 0.0213 mol) was reacted by working in a similar manner to Example 1b).

The thus obtained product (5.2 g) was crystallized from 95° ethanol to yield the desired product (4.8 g).

GC/MS (m/z): 279 (molecular ion), 225 (basic peak)

c) 4-(3-amino-9H-carbazol-9-yl)butanenitrile

The product obtained as described in the preceding step b) (2.3 g, 0.0082 mol) was reacted by working in a similar manner to Example 1c).

The thus obtained product (2.3 g) was purified by flash chromatography by eluting with a mixture of hexane:ethyl acetate=4:6. It was thus obtained the desired product (1.4 g).

1H NMR (300 MHz, DMSO-d$_6$) δ ppm 1.95-2.12 (m, J=7.20, 7.20, 7.20, 7.20 Hz, 2 H), 2.50 (t, J=7.20 Hz, 2 H), 4.33 (t, J=7.16 Hz, 2 H), 4.74 (s, 2 H), 6.84 (dd, J=8.62, 2.19 Hz, 1 H), 7.09 (td, J=7.90, 7.00, 1.00 Hz, 1 H), 7.28 (d, J=1.90 Hz, 1 H), 7.31 (d, J=8.62 Hz, 1 H), 7.36 (td, J=8.22, 7.05, 1.24 Hz, 1 H), 7.48 (d, J=8.30 Hz, 1 H), 7.94 (d, J=7.45 Hz, 1 H).

d) 4-(3-amino-9H-carbazol-9-yl)butanoic acid

The product obtained as described in the preceding step c) (0.7 g, 2.81 mmol) was reacted in water (5 ml) with 95% sulfuric acid (2.8 ml, 50 mmol) at reflux for one night.

Then the reaction mixture was cooled, poured on ice (50 g) and the solid product was collected by filtration. It was thus obtained the desired product (0.83 g), which was used in the next reaction without any further purification.

e) 4-{[3-(2-chlorobenzamido)]-9H-carbazol-9-yl}butanoic acid

The product obtained as described in the preceding step d) (0.3 g, 1.19 mmol) was reacted with 2-chlorobenzoyl chloride (0.171 ml, 1.35 mmol) by working in a similar manner to Example 1d).

The reaction mixture was washed with 1N HCl (3×6 ml). The organic phases were separated. The solvent was removed from the combined organic phases under reduced pressure.

It was thus obtained the 4-{[3-(2-chlorobenzamido)]-9H-carbazol-9-yl}butanoic acid (0.15 g).

1H NMR (300 MHz, DMSO-d$_6$) δ ppm 1.92-2.07 (m, J=7.00, 7.00, 7.00, 7.00 Hz, 2 H), 2.27 (t, J=7.00 Hz, 2 H), 4.41 (t, J=7.14 Hz, 1 H), 7.20 (td, J=7.80, 7.00, 0.80 Hz, 1 H), 7.37-7.80 (m, 9 H), 8.10 (d, J=7.50 Hz, 1 H), 8.57 (d, J=1.83 Hz, 1 H), 10.48 (s, 2 H).

EXAMPLE 15

Preparation of Compound 15

R1=CH$_3$CH$_2$, R2=Cl, X=Y=CH$_3$, R3=R4=R5=R6=H a) 6-bromo-9-ethyl-1,4-dimethyl-3-nitro-9H-carbazole 6-bromo-1,4-dimethyl-3-nitro-9H-carbazole (prepared as described in Chem. Pharm. Bull 35(1), 425-428 (1987), (4.8 g, 0.015 mol) was reacted with iodoethane by working in a similar manner to Example 1a).

The solid product obtained after filtration (5.1 g) was used without any further purification.

1H NMR (300 MHz, DMSO-d$_6$) δ ppm 1.34 (t, J=7.02 Hz, 3 H), 2.83 (s, 3 H), 2.93 (s, 3 H), 4.67 (q, J=7.21 Hz, 2 H), 7.71 (dd, J=8.70, 1.70 Hz, 1 H), 7.77 (d, J=8.50 Hz, 1 H), 7.88 (s, 1 H), 8.38 (d, J=1.75 Hz, 1 H).

b) 6-bromo-9-ethyl-1,4-dimethyl-3-amino-9H-carbazole

The product obtained as described in the preceding step a) (5 g, 0.014 mol) was reacted by working in a similar manner to Example 1c).

The solid product obtained after filtration (5.1 g) was used without any further purification.

GC/MS (m/z): 316, 318 (molecular ion, basic peak)

c) 9-ethyl-1,4-dimethyl-3-amino-9H-carbazole

A solution of the product obtained in the preceding step b) (2 g, 0.006 mol) in THF (25 ml) was added to a suspension of LiAlH$_4$ (0.95 g, 0.025 mol) in anhydrous THF (25 ml). The suspension was refluxed for 24 hours. Afterwards, the suspension was left to cool to room temperature and added with a mixture of H$_2$O and THF 1:1 and NaOH (1.9 g).

THF was removed by evaporation under reduced pressure and the aqueous residue was placed into a separatory funnel and extracted with ethyl acetate (2×50 ml). The organic phase was separated and dried on Na$_2$SO$_4$. The solvent was removed by evaporation under reduced pressure and the thus obtained residue (1.3 g) was used without any further purification.

GC/MS (m/z): 238 (molecular ion), 209 (basic peak).

d) 2-chloro-N-(9-ethyl-1,4-dimethyl-9H-carbazol-3-yl)benzamide

The product obtained as described in the preceding step c) (1.2 g, 0.005 mol) was reacted by working in a similar manner to Example 1d).

The thus obtained product (2 g) was purified by flash chromatography by eluting with a mixture of hexane:ethyl acetate=8:2 and then crystallized from a mixture of chloroform:hexane=1:1.

It was thus obtained the 2-chloro-N-(9-ethyl-1,4-dimethyl-9H-carbazol-3-yl)benzamide (0.2 g).

1H NMR (300 MHz, DMSO-$d_6$) δ ppm 1.32 (t, J=7.00 Hz, 3 H), 2.72 (s, 3 H), 2.79 (s, 3 H), 4.65 (q, J=6.94 Hz, 2 H), 7.17 (s, 1 H), 7.22 (td, J=8.00, 7.00, 0.80 Hz, 1 H), 7.42-7.70 (m, 6 H), 8.21 (d, J=7.93 Hz, 1H), 10.03 (s, 1 H).

EXAMPLE 16

Preparation of Compound 16

R1=CH$_3$CH$_2$, R2=Cl, X=CH3,
R3=R4=R5=R6=Y=H a) 9-ethyl-9H-carbazole

Carbazole (4 g, 0.024 mol) was reacted with iodoethane by working in a similar manner to Example 1a).

The solid product obtained after filtration (4.4 g) was used without any further purification.

1H NMR (300 MHz, DMSO-$d_6$) δ ppm 1.31 (t, J=7.16 Hz, 3 H), 4.44 (q, J=7.02 Hz, 2 H), 7.16-7.23 (m, J=7.90, 7.00, 1.00 Hz, 2 H), 7.45 (td, J=8.30, 7.00, 1.10 Hz, 2 H), 7.60 (d, J=8.18 Hz, 2 H), 8.15 (d, J=7.60 Hz, 2 H).

b) 9-ethyl-3-nitro-9H-carbazole

The product obtained as described in the preceding step a) (4 g, 0.0014 mol) was reacted by working in a similar manner to Example 1b).

The thus obtained product (6 g) was purified by flash chromatography by eluting with a mixture of hexane:ethyl acetate=8:2. It was thus obtained the desired product (2.8 g).

1H NMR (300 MHz, DMSO-$d_6$) δ ppm 1.35 (t, J=7.16 Hz, 3 H), 4.54 (q, J=7.31 Hz, 2 H), 7.34 (ddd, J=8.20, 7.40, 0.80 Hz, 1 H), 7.59 (ddd, J=8.20, 7.30, 1.30 Hz, 1 H), 7.74 (dt, J=8.18, 0.80 Hz, 1 H), 7.80 (d, J=9.06 Hz, 1 H), 8.35 (dd, J=9.06, 2.34 Hz,1 H), 8.41 (dt, J=7.60, 0.80 Hz, 1 H), 9.18 (d, J=2.34 Hz, 1 H).

c) 9-ethyl-4-methyl-3-nitro-9H-carbazole

The product obtained as described in the preceding step b) (2.8 g, 0.0012 mol) was dissolved in anhydrous THF (about 100 ml). The solution was brought at −15° C. in an inert atmosphere. A 3M solution of CH$_3$MgCl in THF (5.7 ml, 0.012 mol) was added and the reaction mixture was kept under stirring for 1 hour at −15° C. Afterwards, DDQ (2,3-dichloro-5,6-dicyano-1,4-benzoquinone) (4.5 g, 0.0020 mol) was added and the reaction mixture was allowed to reach room temperature and maintained under stirring for 48 hours.

The reaction mixture was diluted with dichloromethane (100 ml) and washed with water (2×60 ml). The organic phase was separated and dried on Na$_2$SO$_4$.

The solvent was then removed by evaporation under reduced pressure and the thus obtained residue was purified by flash chromatography by eluting with a mixture of hexane:ethyl acetate=8:2. The pure fractions were combined to give the desired product (0.6 g).

1H NMR (300 MHz, DMSO-$d_6$) δ ppm 1.33 (t, J=7.16 Hz, 3 H), 3.03 (s, 3 H), 4.53 (q, J=7.31 Hz, 2 H), 7.35 (ddd, J=8.18, 7.00, 1.20 Hz, 1 H), 7.59 (ddd, J=8.20, 7.30, 1.20 Hz, 1 H), 7.67 (d, J=9.06 Hz, 1 H), 7.77 (d, J=8.18 Hz, 1 H), 8.10 (d, J=9.06 Hz, 1 H), 8.33 (d, J=8.18 Hz, 1 H).

d) 9-ethyl-4-methyl-9H-carbazol-3-amine

The product obtained as described in the preceding step c) (0.4 g, 0.0016 mol) was reacted by working in a similar manner to Example 1c).

The thus obtained product (0.5 g) was purified by flash chromatography by eluting with a CHCl$_3$. It was thus obtained the desired product (0.3 g).

1H NMR (300 MHz, DMSO-$d_6$) δ ppm 1.24 (t, J=7.02 Hz, 3 H), 2.57 (s, 3 H), 4.32 (q, J=7.02 Hz, 2 H), 4.55 (s, 2 H), 6.91 (d, J=8.48 Hz, 1 H), 7.09 (ddd, J=8.18, 7.00, 1.00 Hz, 1 H), 7.18 (d, J=8.48 Hz, 1 H), 7.35 (ddd, J=8.00, 7.20, 1.20 Hz, 1 H), 7.48 (d, J=8.18 Hz, 1 H), 8.15 (d, J=7.89 Hz, 1 H).

d) 2-chloro-N-(9-ethyl-4-methyl-9H-carbazol-3-yl)benzamide

The product obtained as described in the preceding step d) (0.3 g, 0.0013 mol) was reacted by working in a similar manner to Example 1d).

The thus obtained product (0.5 g) was crystallized 2 times from a mixture of hexane:ethyl acetate=1:2. It was thus obtained the 2-chloro-N-(9-ethyl-4-methyl-9H-carbazol-3-yl)benzamide (0.23 g).

1H NMR (300 MHz, DMSO-$d_6$) δ ppm 1.31 (t, J=7.10 Hz, 3 H), 2.77 (s, 3 H), 4.47 (q, J=7.05 Hz, 2 H), 7.23 (ddd, J=8.00, 7.00, 1.00 Hz, 1 H), 7.39-7.72 (m, 8 H), 8.23 (d, J=7.93 Hz, 1 H), 10.09 (s, 1 H).

EXAMPLES 17 AND 18

Preparation of Compounds 17 and 18

Compounds 17 and 18 may be prepared by working in a manner similar to that described in Examples 1-16 above.

EXAMPLE 19

Preparation of Comparative Compound A

R1=CH$_3$CH$_2$, R2=OH, R3=R4=R5=R6=X=Y=H a) N-(9-ethyl-9H-carbazol-3-yl)-2-methoxybenzamide 3-Amino-9-ethylcarbazole (5.6 g; 0.027 mol) was reacted with 2-methoxybenzoyl chloride (4.35 ml; 0.029 mol) by working in a manner similar to that described in Example 4.

The residue thus obtained (3.5 g) was crystallized from isopropanol to give the desired product (2.5 g).

$^1$H NMR (300 MHz, DMSO-$d_6$) δ ppm 1.32 (t, J=7.1 Hz, 3 H), 3.96 (s, 3H), 4.43 (q, J=7.1 Hz, 2 H), 7.10 (td, J=7.4, 1.0 Hz, 1 H), 7.15-7.24 (m, 2 H), 7.41-7.48 (m, 1 H), 7.48-7.55 (m, 1 H), 7.55-7.61 (m, 2 H), 7.70-7.79 (m, 2 H), 8.10 (d, J=7.6 Hz, 1 H), 8.58 (d, J=1.8 Hz, 1 H), 10.13 (br, s, 1 H).

b) N-(9-ethyl-9H-carbazol-3-yl)-2-hydroxybenzamide

To a solution containing boron tribromide (1M in dichloromethane, 0.2 ml; 0.001 mol) in dichloromethane (10 ml) was added the product obtained as described in step a) above (0.5 g; 0.001 mol). The mixture thus obtained was stirred for 16 hours.

The reaction mixture was transferred into a separating funnel and washed with $H_2O$ (2×50 ml). The organic phase was separated out and dried over $Na_2SO_4$. The solvent was removed by evaporation under reduced pressure and the residue thus obtained (0.4 g) was crystallized from ethanol.

N-(9-Ethyl-9H-carbazol-3-yl)-2-hydroxybenzamide (0.25 g) was thus obtained.

$^1$H NMR (300 MHz, DMSO-$d_6$, 70° C.), δ ppm 1.37 (t, J=7.1 Hz, 3 H), 4.45 (q, J=7.1 Hz, 2 H), 5.55 (br, s, 1 H), 6.94-7.02 (m, 2 H), 7.21 (t, J=7.0 Hz, 1 H), 7.41-7.77 (m, 5 H), 8.04-8.15 (m, 2 H), 8.42-8.48 (m, 1 H), 10.33 (br, s, 1 H).

EXAMPLE 20

Preparation of Comparative Compound B
(R1=CH$_3$CH$_2$, R2=SCH$_3$, R3=R4=R5=R6=X=Y=H)

Comparative Compound B was prepared in a manner similar to that described with respect to Compounds 6-9, starting with 9-ethyl-3-aminocarbazole and 2-methylmercaptobenzoic acid.

LC/MS (M+H)$^+$=361.2.

EXAMPLE 21

Test of In Vitro Activity

This test allows evaluation of the inhibitory capability on the production of the PGE$_2$ prostaglandins and the selectivity relative to the production of the PGF$_{2\alpha}$ prostaglandins.

The cell line A549, human pulmonary adenocarcinoma, was used, which is particularly sensitive to stimulation with pro-inflammatory cyokines, for instance IL-1$_\beta$, and, in response to this stimulation, is particularly active in the production and release of two prostanoids: PGE$_2$ and PGF$_{2\alpha}$ (Thoren S. Jakobsson P-J, 2000).

The cells were stimulated with IL-1$_\beta$, (1 ng/ml) and simultaneously treated with the test compound for 18 hours in an appropriate culture medium (DMEM—Dulbecco's Modified Eagle's Medium) supplemented with 5% foetal calf serum and L-glutamine (4 mM final) in an incubator at 37° C. and at a $CO_2$ concentration of 5%.

After the incubation, the amount of PGE$_2$ and PGF$_{2\alpha}$ produced and released into the supernatant were assayed using an EIA kit (produced and sold by Cayman Chemicals, Ann Arbor, Mich., USA).

The comparative compounds used were indomethacin (Sigma-Aldrich), a non-steroidal anti-inflammatory drug that inhibits in equal measure both PGE$_2$ and PGF$_{2\alpha}$, and also the compounds of formula (I) in which R1=CH$_3$CH$_2$, R2=OH, R3=R4=R5=R6=X=Y=H (comparative compound A) and R1=CH$_3$CH$_2$, R2=SCH$_3$, R3=R4=R5=R6=X=Y=H (comparative compound B).

The results, given as percentages of inhibition of the production of PGE$_2$ and of PGF$_{2\alpha}$ at a concentration of 10 μm, are shown in Table 2.

TABLE 2

| | % inhibition at 10 μM | |
|---|---|---|
| Compound | PGE$_2$ | PGF$_{2\alpha}$ |
| 1 | 59 | 27 |
| 2 | 90 | 66 |
| 3 | 86 | 7 |
| 4 | 67 | 0 |
| 5 | 93 | 60 |

TABLE 2-continued

| | % inhibition at 10 μM | |
|---|---|---|
| Compound | PGE$_2$ | PGF$_{2\alpha}$ |
| 6 | 76 | 26 |
| 7 | 90 | 48 |
| 8 | 77 | 16 |
| A | 88 | 84 |
| B | na | na |
| indomethacin | 100 | 100 | na = not active at the experimental concentration

For illustrative purposes, Table 3 shows the pIC$_{50}$ values of certain compounds of the invention, where pIC$_{50}$ is the negative logarithm of the IC$_{50}$ value, which, in turn, is the concentration of compound that inhibits 50% of the production of PGE$_2$ or of PGF$_{2\alpha}$ relative to cells that have been stimulated but not treated with the same compound.

TABLE 3

| | pIC$_{50}$ | |
|---|---|---|
| Compound | PGE$_2$ | PGF$_{2\alpha}$ |
| 2 | 6.1 | 5 |
| 3 | 5.9 | <4 |
| 4 | 6.2 | 4 |
| 6 | 6.4 | <4 |
| 7 | 5.7 | <4 |
| 8 | 5.4 | <4 |
| indomethacin | 8.3 | 8.6 |

EXAMPLE 22

Test of In Vivo Activity

This test allows evaluation of the activity of the compounds of the invention in a nociceptive test of inflammatory origin.

The test compounds were evaluated in an experimental model that causes stretching induced with acetic acid in mice (Stock J. L. et al., J. Clin. Inv. 2001, 107: 325-331). Female CD-1 mice weighing 25-30 g were used for the test.

The animals were treated orally with the compound (30 mg/kg) suspended in methylcellulose (MTC). The control animals were treated orally with the vehicle alone (MTC).

One hour after treatment, an intraperitoneal injection of acetic acid (0.7% v/v in physiological saline, 16 μl/g of body weight) was given to the animals to induce inflammatory pain and to check the effects of the treatment on the nociceptive response.

Immediately after the administration of acetic acid and for the following 20 minutes the number of stretches was measured, which represents the parameter for evaluation of the nociceptive response.

The animals treated with the compounds of the invention showed a significant reduction in stretching in the 20 minutes following the administration of acetic acid, compared with the animals treated with MTC alone.

The results obtained with Compound 4 are shown in FIG. 1.

EXAMPLE 23

Test on Human Primary Endothelial Cells (HUVEC)

This test allows evaluation of the capability of the compounds of the invention to inhibit the production of PGI$_2$.

The absence of inhibitory activity on this prostanoid can ensure maintenance of the vasoprotective action of the $PGI_2$ prostanoids and provide useful pharmacological information regarding the absence of adverse side effects on the endothelium.

The action of the test compounds is evaluated in HUVEC cells under basal conditions and conditions of stimulation (J. Immunol. 1989, Jun. 1; 142(11): 3993-9).

The results are given as a percentage of inhibition relative to the control enzymatic activity.

Indomethacin is used as reference compound.

The compounds of the invention did not show any significant inhibition of secretion of $PGI_2$.

The results are shown in Table 4.

TABLE 4

| Compound | LogM | Inhibition (%) | Comparison Compound | $IC_{50}$ |
|---|---|---|---|---|
| 2 | −5 | 31 | indomethacin | −8.0 |
| 4 | −5 | 21 | indomethacin | −8.0 |
| 6 | −5 | 15 | indomethacin | −8.0 |
| 7 | −5 | 30 | indomethacin | −8.0 |

The invention claimed is:

1. A 3-aminocarbazole, or a pharmaceutically acceptable salt thereof, selected from the compounds of Table 1 below:

TABLE 1

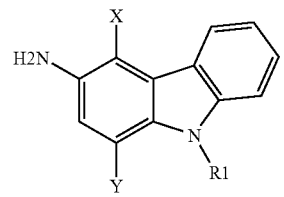

(I)

| Compound No. | R1 | R2 | R3 | R4 | R5 | R6 | X | Y |
|---|---|---|---|---|---|---|---|---|
| 3 | $PhCH_2$ | Cl | H | H | H | H | H | H |
| 4 | $CH_3CH_2$ | $CF_3$ | H | H | H | H | H | H |
| 5 | $CH_3CH_2$ | $CH_3$ | H | H | H | $CH_3$ | H | H |
| 6 | $CH_3CH_2$ | F | H | H | H | $CF_3$ | H | H |
| 7 | $CH_3CH_2$ | $CF_3$ | H | F | H | H | H | H |
| 8 | $CH_3CH_2$ | Br | H | H | H | $OCH_3$ | H | H |
| 9 | $CH_3CH_2$ | Cl | H | H | Cl | $OCH_3$ | H | H |
| 10 | $PhCH_2$ | $NH_2$ | H | H | H | H | H | H |
| 11 | $CH_3CH_2$ | $N(CH_3)_2$ | H | H | H | H | H | H |
| 12 | $CH_3(CH_2)_4$ | Cl | H | H | H | H | H | H |
| 13 | $CH_3OCH_2CH_2$ | Cl | H | H | H | H | H | H |
| 14 | $HOOC(CH_2)_3$ | Cl | H | H | H | H | H | H |
| 15 | $CH_3CH_2$ | Cl | H | H | H | H | $CH_3$ | $CH_3$ |
| 18 | $CH_3CH_2$ | Cl | H | H | H | H | $CH_3$ | $OCH_3$. |

2. A composition, comprising the 3-aminocarbazole, or its salt, of claim 1 and least one pharmaceutically acceptable inert vehicle.

3. A method of treating a disease selected from the group consisting of Alzheimer's disease, atherosclerosis, and a combination thereof, in a person in need thereof, the method comprising administering to the person in need thereof, in an amount sufficient to treat the disease, a 3-aminocarbazole of formula (I), or a pharmaceutically acceptable salt thereof, selected from the compounds of Table 2 below:

TABLE 2

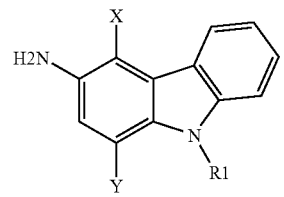

(I)

| Compound No. | R1 | R2 | R3 | R4 | R5 | R6 | X | Y |
|---|---|---|---|---|---|---|---|---|
| 1 | $CH_3$ | Cl | H | H | H | H | H | H |
| 2 | $CH(CH_3)_2$ | Cl | H | H | H | H | H | H |
| 3 | $PhCH_2$ | Cl | H | H | H | H | H | H |
| 4 | $CH_3CH_2$ | $CF_3$ | H | H | H | H | H | H |
| 5 | $CH_3CH_2$ | $CH_3$ | H | H | H | $CH_3$ | H | H |
| 6 | $CH_3CH_2$ | F | H | H | H | $CF_3$ | H | H |
| 7 | $CH_3CH_2$ | $CF_3$ | H | F | H | H | H | H |
| 8 | $CH_3CH_2$ | Br | H | H | H | $OCH_3$ | H | H |
| 9 | $CH_3CH_2$ | Cl | H | H | Cl | $OCH_3$ | H | H |
| 10 | $PhCH_2$ | $NH_2$ | H | H | H | H | H | H |
| 11 | $CH_3CH_2$ | $N(CH_3)_2$ | H | H | H | H | H | H |
| 12 | $CH_3(CH_2)_4$ | Cl | H | H | H | H | H | H |
| 13 | $CH_3OCH_2CH_2$ | Cl | H | H | H | H | H | H |
| 14 | $HOOC(CH_2)_3$ | Cl | H | H | H | H | H | H |
| 15 | $CH_3CH_2$ | Cl | H | H | H | H | $CH_3$ | $CH_3$ |
| 16 | $CH_3CH_2$ | Cl | H | H | H | H | $CH_3$ | H |
| 17 | $CH_3CH_2$ | Cl | H | H | H | H | H | $CH_3$ |
| 18 | $CH_3CH_2$ | Cl | H | H | H | H | $CH_3$ | $OCH_3$. |

4. A method for preparing the 3-aminocarbazole, or pharmaceutically acceptable salt thereof, of claim 1, the method comprising
 a) reacting of an amine of formula (II)

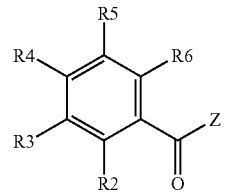

(II)

wherein R1, X and Y have the meanings indicated in said Table 1, with a compound of formula (III)

(III)

wherein R2, R3, R4, R5 and R6 have the meanings indicated in said Table 1, and
Z is selected from Cl, Br, OH, OR and OC(O)R, wherein R is a linear or branched alkyl comprising from 1 to 6 carbon atoms, to give a 3-aminocarbazole compound of formula (I)

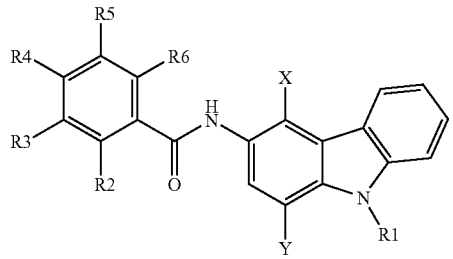

in which R1, R2, R3, R4, R5, R6, X and Y have the meanings indicated in said Table 1, and b) optionally, forming a pharmaceutically acceptable salt of the compound of formula (I).

5. The method of claim 4, comprising forming a pharmaceutically acceptable salt of the compound of formula (I).

6. The method of claim 4, wherein the method does not comprise forming a pharmaceutically acceptable salt of the compound of formula (I).

7. The 3-aminocarbazole of claim 1, that is not a salt.

8. The pharmaceutically acceptable salt of the 3-aminocarbazole of claim 1.

9. A method of inhibiting the production of prostaglandin $E_2$ in a person in need thereof, the method comprising administering to the person in need thereof, in an amount sufficient to inhibit the production of prostaglandin $E_2$, a 3-aminocarbazole of formula (I), or pharmaceutically acceptable salt thereof, selected from the compounds of Table 3 below:

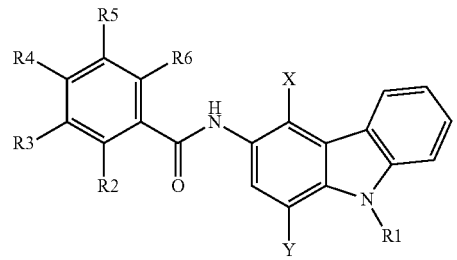

| Compound No. | R1 | R2 | R3 | R4 | R5 | R6 | X | Y |
|---|---|---|---|---|---|---|---|---|
| 1 | CH₃ | Cl | H | H | H | H | H | H |
| 2 | CH(CH₃)₂ | Cl | H | H | H | H | H | H |
| 3 | PhCH₂ | Cl | H | H | H | H | H | H |
| 4 | CH₃CH₂ | CF₃ | H | H | H | H | H | H |
| 5 | CH₃CH₂ | CH₃ | H | H | H | CH₃ | H | H |
| 6 | CH₃CH₂ | F | H | H | H | CF₃ | H | H |
| 7 | CH₃CH₂ | CF₃ | H | F | H | H | H | H |
| 8 | CH₃CH₂ | Br | H | H | H | OCH₃ | H | H |
| 9 | CH₃CH₂ | Cl | H | H | Cl | OCH₃ | H | H |
| 10 | PhCH₂ | NH₂ | H | H | H | H | H | H |
| 11 | CH₃CH₂ | N(CH₃)₂ | H | H | H | H | H | H |
| 12 | CH₃(CH₂)₄ | Cl | H | H | H | H | H | H |
| 13 | CH₃OCH₂CH₂ | Cl | H | H | H | H | H | H |
| 14 | HOOC(CH₂)₃ | Cl | H | H | H | H | H | H |
| 15 | CH₃CH₂ | Cl | H | H | H | H | CH₃ | CH₃ |
| 16 | CH₃CH₂ | Cl | H | H | H | H | CH₃ | H |
| 17 | CH₃CH₂ | Cl | H | H | H | H | H | CH₃ |
| 18 | CH₃CH₂ | Cl | H | H | H | H | CH₃ | OCH₃. |

10. The 3-aminocarbazole of claim 1, or pharmaceutically acceptable salt thereof, which is Compound 8 or a pharmaceutically acceptable salt thereof.

11. The method of claim 3, wherein the 3-aminocarbazole of formula (I) is Compound 1, or pharmaceutically acceptable salt thereof.

12. The method of claim 9, wherein the person in need thereof has Alzheimer's disease.

13. The method of claim 9, wherein the person in need thereof has atherosclerosis.

14. The method of claim 9, wherein the person in need thereof has Alzheimer's disease and atherosclerosis.

15. The method of claim 3, wherein the 3-aminocarbazole of formula (I) is Compound 2, or pharmaceutically acceptable salt thereof.

16. The 3-aminocarbazole of claim 1, or pharmaceutically acceptable salt thereof, which is Compound 3 or a pharmaceutically acceptable salt thereof.

17. The 3-aminocarbazole of claim 1, or pharmaceutically acceptable salt thereof, which is Compound 4 or a pharmaceutically acceptable salt thereof.

18. The 3-aminocarbazole of claim 1, or pharmaceutically acceptable salt thereof, which is Compound 5 or a pharmaceutically acceptable salt thereof.

19. The 3-aminocarbazole of claim 1, or pharmaceutically acceptable salt thereof, which is Compound 6 or a pharmaceutically acceptable salt thereof.

20. The 3-aminocarbazole of claim 1, or pharmaceutically acceptable salt thereof, which is Compound 7 or a pharmaceutically acceptable salt thereof.

21. The method of claim 3, wherein the 3-aminocarbazole of formula (I) is Compound 16, or pharmaceutically acceptable salt thereof.

22. The method of claim 3, wherein the 3-aminocarbazole of formula (I) is Compound 17, or pharmaceutically acceptable salt thereof.

* * * * *